(12) United States Patent
Myers

(10) Patent No.: US 6,826,287 B2
(45) Date of Patent: Nov. 30, 2004

(54) EARMUFF WITH CONTROLLED LEAK

(75) Inventor: Brian Myers, Indianapolis, IN (US)

(73) Assignee: Cabot Safety Intermediate Corporation, Southbridge, MA (US)

( * ) Notice: Subject to any disclaimer, the term of this patent is extended or adjusted under 35 U.S.C. 154(b) by 76 days.

(21) Appl. No.: 09/829,159

(22) Filed: Apr. 9, 2001

(65) Prior Publication Data

US 2002/0146142 A1 Oct. 10, 2002

(51) Int. Cl.[7] .............................................. H04R 25/00
(52) U.S. Cl. ........................ 381/373; 381/370; 381/72
(58) Field of Search ................................ 381/372, 373, 381/72, 74, 371, 370; 181/173, 175, 129, 135; 128/866, 868; 2/208, 209, 616

(56) References Cited

U.S. PATENT DOCUMENTS

| | | | |
|---|---|---|---|
| 2,476,224 A | * | 7/1949 | Rosenblatt .................. 128/868 |
| 3,335,720 A | | 8/1967 | Aileo |
| 3,637,040 A | | 1/1972 | Gorman |
| 4,529,057 A | | 7/1985 | Telford |
| 4,833,719 A | * | 5/1989 | Carme et al. .................. 381/72 |
| 4,922,542 A | * | 5/1990 | Sapiejewski ................ 381/372 |
| 5,134,659 A | * | 7/1992 | Moseley ...................... 381/72 |

FOREIGN PATENT DOCUMENTS

GB        806844        7/1957

* cited by examiner

*Primary Examiner*—Suhan Ni
(74) *Attorney, Agent, or Firm*—Cantor Colburn LLP

(57) ABSTRACT

An acoustic earmuff device is provided comprising a rigid cup, including inner and outer surfaces, a sound channel means disposed through said cup shaped portion, and a plate means operatively associated with said sound channel means, such that when the plate means is in a first orientation, sound attenuation through the plate means is greater than when the plate means is in a second orientation.

14 Claims, 4 Drawing Sheets

EARMUFF WITH CONTROLLED LEAK

BACKGROUND

The use of earplugs and earmuffs are the two most useful ways to protect against hearing loss in those environments where noise levels are not able to be controlled within safe limits. In many of those areas, the use of earmuffs is the preferred means of reducing sound intensity, in most instances to a degree even greater than that provided by the use of earplugs. Other uses for noise excluding hearing protectors include producing quiet for study, sleep, or audio purposes.

Earmuffs have advantages for intermittent use where continuous insertion and removal of earplugs would be annoying or impractical. Also, earmuffs tend to deliver higher in-field noise protection in many noisy environments than most earplugs. Additional preference for earmuffs include use outdoors in cool weather and use in dry climates.

Many earmuff wearers lift the muff cup off the ear when communicating with co-workers. Unfortunately, this action results in momentary removal of protection from the ear. Although the time can be minimal, the additive effects throughout the workday can be a concern. Additionally, improper re-seating of the earmuff around the ear can be a concern.

SUMMARY

The above described and other disadvantages are overcome by the present acoustic earmuff device, which comprises a rigid cup, including inner and outer surfaces, a sound channel means disposed through said cup shaped portion, and a plate means operatively associated with said sound channel means, such that when the plate means is in a first orientation, sound attenuation through the plate means is greater than when the plate means is in a second orientation.

The above described and other features are exemplified by the following figures and detailed description.

BRIEF DESCRIPTION OF DRAWINGS

Referring now to the figures wherein the like elements are numbered alike.

DETAILED DESCRIPTION

Figure 1:
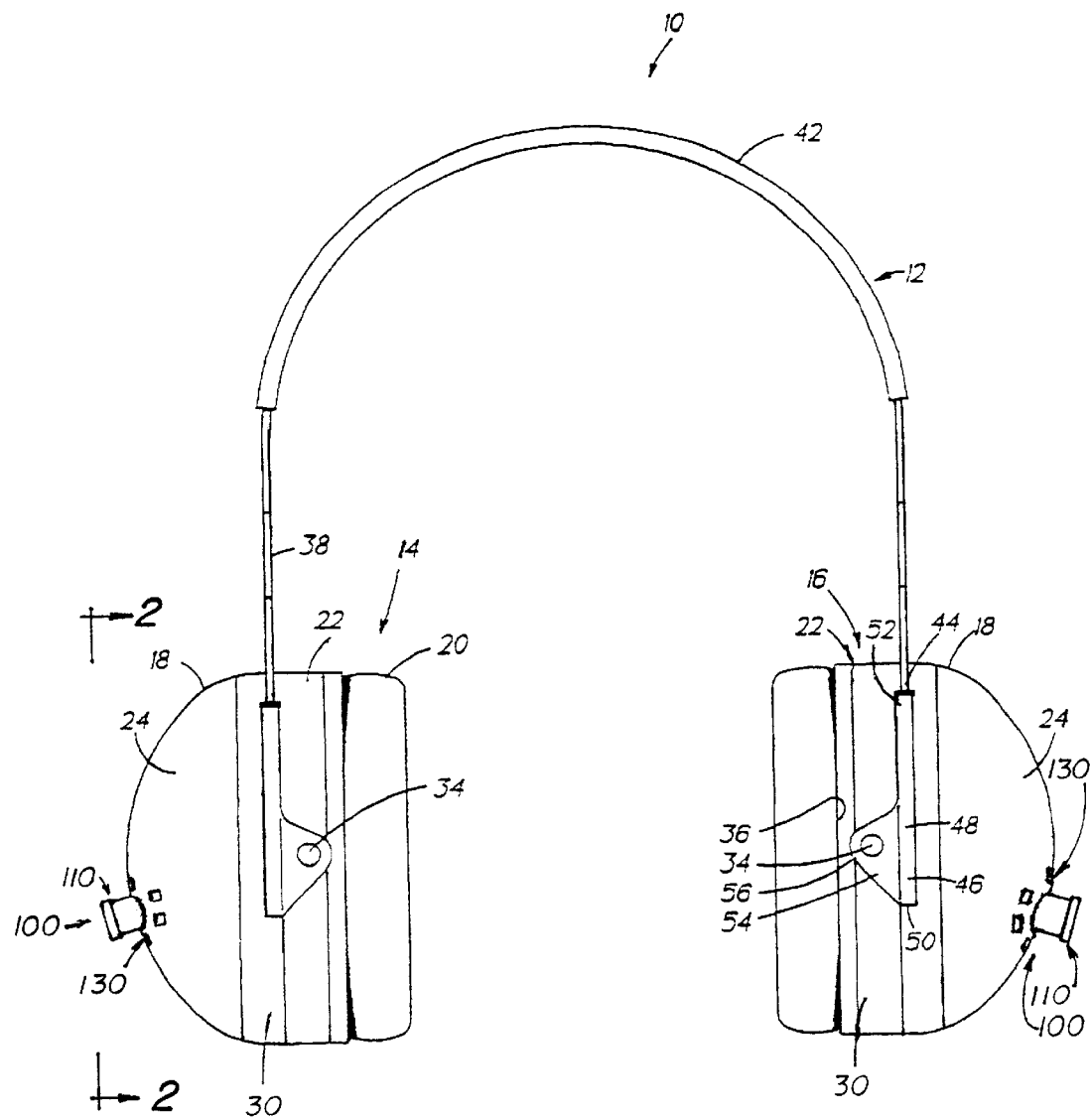
FIG. 1 is a side elevation view of an exemplary acoustic earmuff device of the present invention.

Referring now to FIG. 1, an exemplary earmuff device is shown generally at 10 and broadly comprises a generally U-shaped, resilient connecting band 12 and a pair of acoustic earmuff cup assemblies 14 and 16 connected to opposite ends of connecting band 12.

Figure 3:
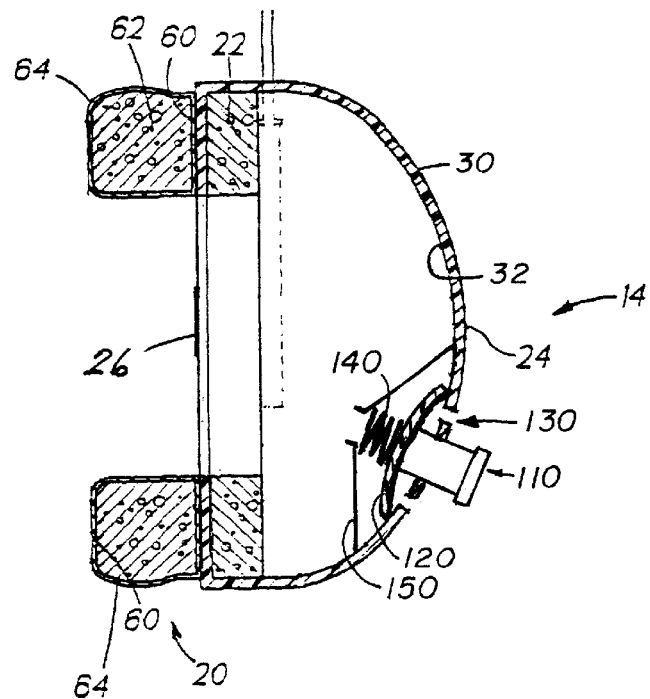
FIG. 3 is a cross-section of line 3—3 of FIG. 2.
Figure 4:
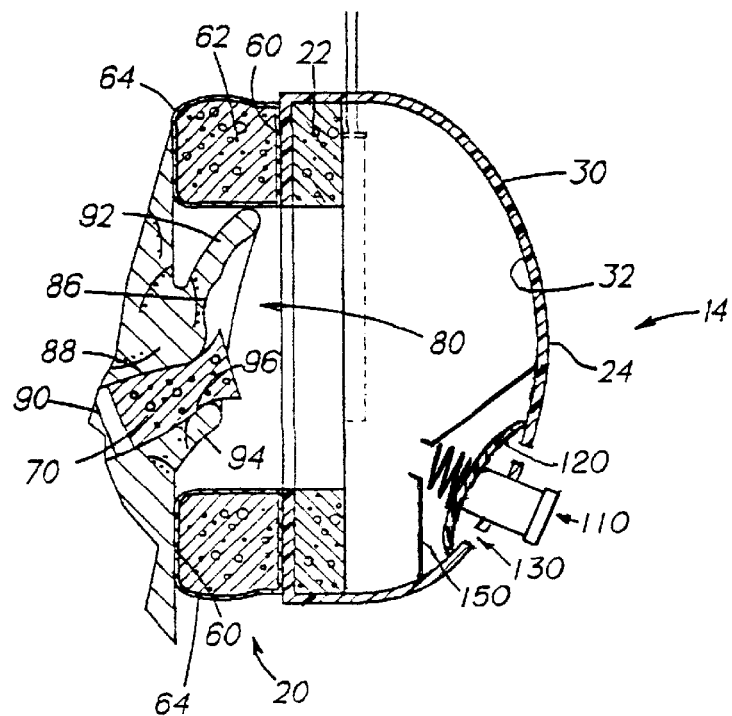
FIG. 4 is a cross section through an exemplary earmuff cup of the present invention showing an earplug disposed within the earmuff cup and inserted within a wearer's ear.

Each of acoustic earmuff cup assemblies 14 and 16 comprises a rigid cup 18, a foam cushion 20, and optionally an earmuff cup liner 22. With reference to FIGS. 3–4, rigid cup 18 generally comprises of two pieces: a cup shaped portion 24 and a cushion seal plate 26 that operatively communicate at an interface. Cup shaped portion 24 is shown with an outer surface 30 and an inner surface 32. In the exemplary embodiment shown in FIG. 1, cup shaped portion 24 includes a pair of spaced retaining pins 34 which extend outwardly from outer surface 30. Preferably, retaining pins 34 are spaced about 180° from one another and are centrally located around a peripheral edge 36 of cup shaped portion 24. It being understood that retaining pins 34 may have a variety of cross-sectional shapes and in the exemplary embodiment shown, retaining pins 34 are generally circular in shape.

Figure 2:
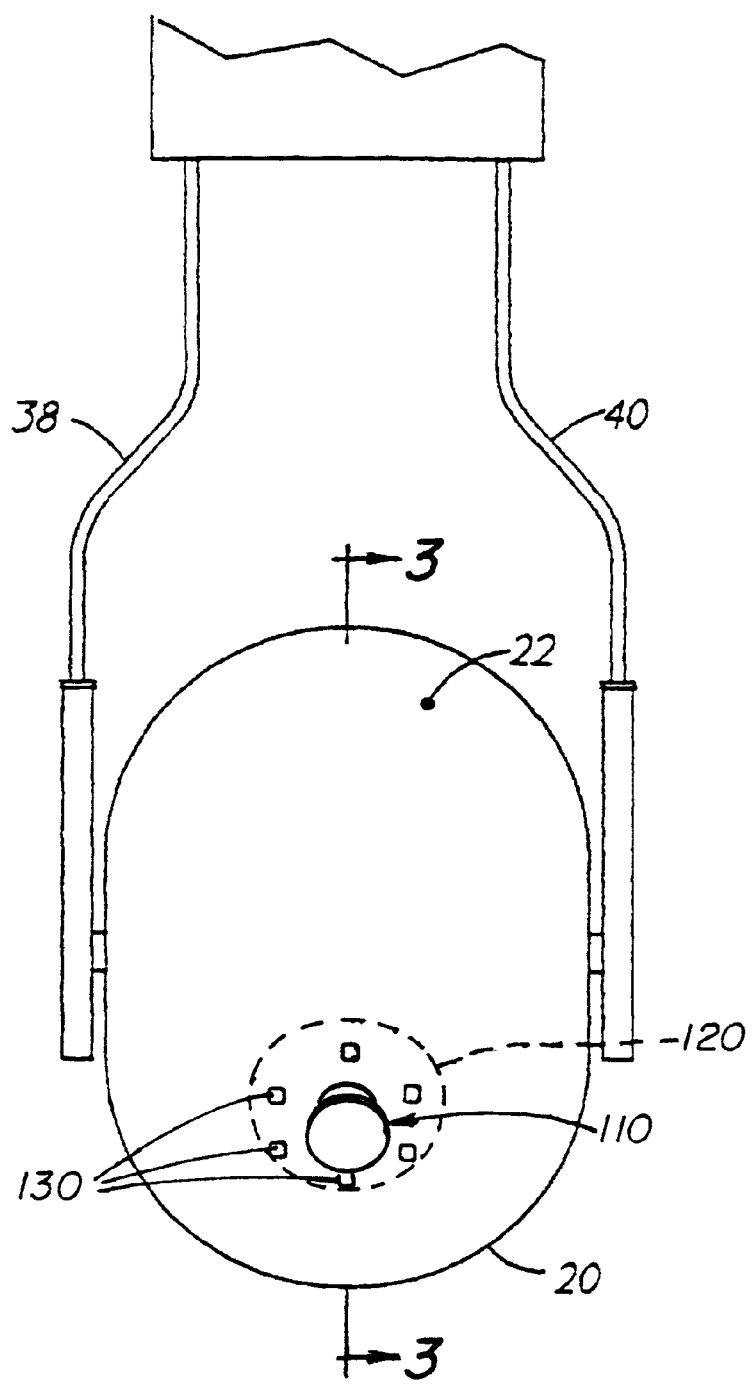
FIG. 2 is a front elevation view of the exemplary acoustic earmuff device of FIG. 1 looking in the direction of arrow 2 in FIG. 1.

In the exemplary embodiments shown in FIGS. 1–2, connecting band 12 comprises two resilient wires 38 and 40 held in a generally parallel alignment by a strip 42 of flexible material, such as a rubber or a plastic. Each end 44 of resilient wires 38 and 40 includes a connector member 46 which includes a base portion 48 having a central opening 50 extending therethrough. Central opening 50 receives end 44 of one of wires 38 and 40 so that end 44 is retained within central opening 50 of base portion 48. Formed within central opening 50 at an upper end 52 is a stopper (not shown) which permits end 44 of resilient wire 38 or 40 to freely move within central opening 50 but prevents end 44 from being removed from central opening 50 at upper end 52.

The exemplary connecting member 46 illustrated by FIG. 1 has an ear 54 extending from base portion 48, wherein ear 54 has an opening 56 which is sized to receive retaining pin 34 so that ear 54 engages and retains pin 34. As a result, ends 44 of wires 38 and 40 are secured to earmuff cup assemblies 14, 16 by the operative association of the connector member 46 and retaining pin 34. It will now be understood that end 44 is free to slide within central opening 50 so that earmuff 14, 16 may be slidably adjusted with respect to connecting band 12 so as to dispose them around the ears and resiliently against the head of a wearer. The illustrated connecting band 12 is solely exemplary and merely illustrates one of many types of connecting bands 12 which may be used.

Referring to FIGS. 1 and 2, an exemplary embodiment further includes a means for selectively permitting cup leak for communication purposes, shown generally at 100. In an exemplary embodiment, the means for selectively permitting cup leak 100 is a means for creating a small leak when a wearer desires momentary decreased attenuation for listening purposes. In one exemplary embodiment, the cup leak means 100 comprises an actuation means, shown generally at 110, operatively associated with a plate means (shown generally as 120 in FIGS. 3–4), which is selectively associated with a sound channel means, shown generally at 130. Manipulation of the actuation means 110 preferably urges the plate means 120 to a position which allows cup leak or decreased attenuation via the sound channel means 130. The actuation means 110 may take one of many structural configurations, including but not limited to buttons, posts, threaded posts, notched posts, screws, pins, plungers, electric or magnetic switches or any other equivalent as is known in the art of buttons and switches. The plate means 120 may take any structure which may be selectively associated with the sound channel means, including but not limited to, circular plates, concave or convex surfaces, notched surfaces, grooved surfaces and irregular surfaces, among others. While the plate means 120 is preferably disposed on the interior surface 32 of the cup shaped portion 24, the plate means 120 may also be disposed on the exterior 30 of the cup shaped portion 24 or between the interior 32 and exterior 30 surfaces of the cup shaped portion 24. The plate means 120 may also be any material which attenuates or blocks sound, including plastics, metals, foams, or elastomers, among others.

Preferably, the plate means 120 is initially biased in a configuration that it is associated with the sound channel means 130 such that cup leak does not occur or sound attenuation is not decreased. The actuation means 110 is thus preferably manipulated such that the plate means 120 is not associated with the sound channel means such that cup leak does occur or sound attenuation is decreased. It is similarly preferred that manipulation of the actuation means 110 be by depression of the actuation means, contact of two portions of the actuation means together, rotation of the actuation means or in any other manner which causes the plate means 120 to not be associated with the sound channel means such that cup leak occurs or sound attenuation is decreased. The sound channel means 130 may be an interruption in the ear cup which provides at least a partially open pathway for cup leak or sound attenuation decrease. The interruption may be a hole, cut or other opening through the material of the cup, or it may be material having a lesser attenuation efficiency, the material provided at least partially between the interior and the exterior of the cup. The interruption may also be a combination of a hole, cut or other opening with a material having a lesser attenuation efficiency.

Referring again to FIGS. 3 and 4, an exemplary embodiment of means for selectively permitting cup leak is shown. The cup shaped portion 24 includes inner 32 and outer surfaces 34. A sound channel means 130 is shown as a perforation through the cup shaped portion 24. The actuation means 110 is shown as a plunger type button extending through the cup shaped portion 24 and is operatively associated with a first side of plate means 120. As is preferred, the plate means 120 is initially biased by a biasing means 140 such that the sound channel or area around the sound channel is substantially blocked, closed or otherwise covered with a sound attenuating or sound proof material. In the shown embodiment, the biasing means 140 is a spring material operatively associated with the plate means and a support structure 150 on or within the cup shaped portion 24. The biasing means 140 may also be a foam, magnet, elastomer, stretchy material, other resilient member, combinations of the foregoing or equivalents thereof. Thus, until the actuation means 110 is actuated, cup leak does not occur and sound attenuation is not substantially decreased.

Referring still to FIGS. 3 and 4, an exemplary cushion 20 generally comprises a plurality of thin sheets of flexible polyvinyl chloride or polyurethane, one of the sheets being vacuum formed 60 and filled with a foam 62 or a liquid, then thermally bonded to a second sheet 64, after which the trim is cut off. The illustrated cushion 20 is solely exemplary and merely illustrates one of many types of cushions 20 which may be used. It is preferred that the cushion 20 assume a shape such that it generally fits the earmuff cup 14, 16 design in a reasonable manner. However, the shape of cushion 20 may be any shape, e.g. cylindrical, round, rectangular, irregular. The exemplary cushion 20 is quite flexible and may also be made to a shape requiring deformation to fit earmuff cup assemblies 14, 16. Cushion 20 defines a central opening 21 which generally has a shape which matches the shape of cushion 20. Opening 21 is generally aligned with the internal portions of an ear, as shown and described in reference to FIG. 4, when earmuff device 10 is worn and covers the ear.

One exemplary and preferred cushion 20 is disclosed in commonly assigned U.S. Pat. No. 5,420,381 to Gardner Jr. et al., which is hereby incorporated in its entirety.

Optional earmuff cup liner 22 generally comprises an open cell foam or other material containing open pores of size and shape to absorb high frequency sound of about 1000 to about 8000 Hertz. Polyurethane open-celled acoustical foam is a particularly preferred choice because of its low cost and low density. As illustrated by the exemplary embodiments of FIGS. 3 and 4, earmuff cup liner 22 defines a central opening 25 similar to opening 21 defined by cushion 20. Preferably, opening 21 has diameter similar to that of opening 25.

Figure 5:
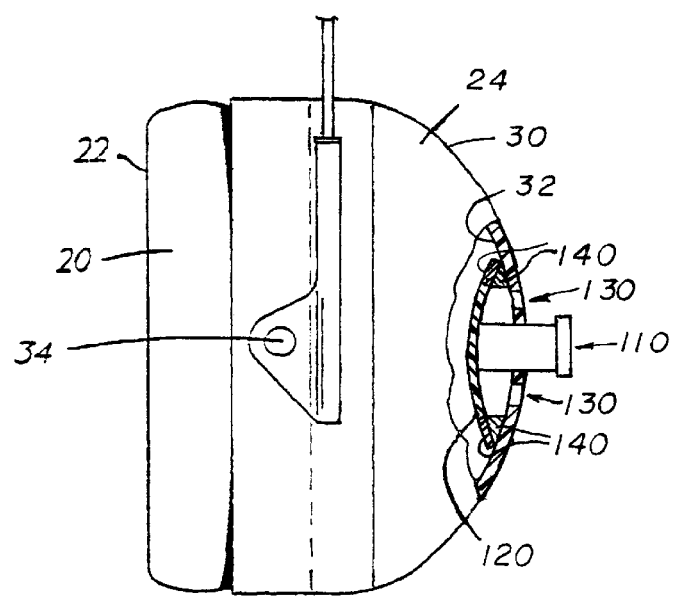
FIG. 5 is a side elevation view of an acoustic earmuff cup according to a another embodiment of the present invention.

Referring now to FIG. 5, another exemplary embodiment of means for selectively permitting cup leak is shown. The cup shaped portion 24 includes inner 32 and outer surfaces 34. A sound channel means 130 is shown as a perforation through the cup shaped portion 24. The actuation means 110 is shown as a plunger type button extending through the cup shaped portion 24 and is operatively associated with a first side of plate means 120. As is preferred, the plate means 120 is initially biased by a biasing means 140 such that the sound channel or area around the sound channel is substantially blocked, closed or otherwise covered with a sound attenuating or sound proof material. In the shown embodiment, the biasing means 140 is magnetic. While magnets are shown on both the plate means 120 and the cup shaped portion 24, where either of the plate means 120 or cup shaped portion 24 comprises a material with an affinity for magnetic materials, the biasing means 140 may reside in either the plate means 120 or the cup shaped portion 24 or both. Thus, until the actuation means 110 is actuated, cup leak does not occur and sound attenuation is not substantially decreased.

Figure 6:
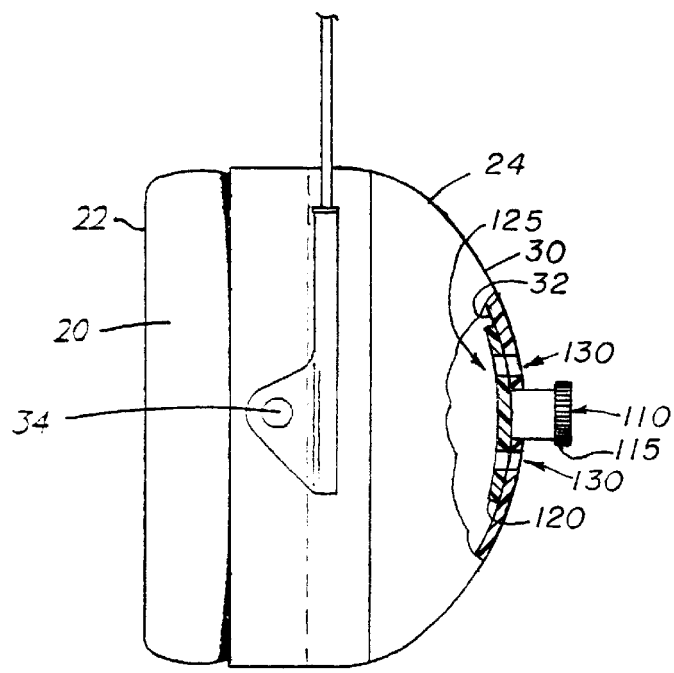
FIG. 6 is a side elevation view of an acoustic earmuff cup according to a another embodiment of the present invention.

Referring now to FIG. 6, another exemplary embodiment of means for selectively permitting cup leak is shown. The cup shaped portion 24 includes inner 32 and outer surfaces 34. A sound channel means 130 is shown as a perforation through the cup shaped portion 24. The actuation means 110 is shown as a rotation type post extending through the cup shaped portion 24 and is operatively associated with a first side of plate means 120. As is preferred, the actuation means 110 includes a means for improving grip 115, shown in FIG. 6 as a series of grooves around a first end of the actuation means 110. The plate means includes areas of reduced sound attenuation 125, which may be perforations, slits, holes or the equivalent, or be areas of material having lower degrees of sound attenuation such that when the actuation means 110 and plate means 120 are in a second orientation, sound attenuation through the plate means 120 is less than when the actuation means 110 and plate means 120 are in a first orientation. The plate means 120 may optionally initially be biased by a biasing means (not shown) such that the sound channel or area around the sound channel is substantially blocked, closed or otherwise covered with a sound attenuating or sound proof material.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An acoustic earmuff device, comprising:

a rigid cup having a cup shaped portion including inner and outer surfaces;

a sound channel means disposed through said cup shaped portion;

an actuation means operatively associated with said plate means; and a plate means operatively associated with said sound channel means, such that when said plate means is in a first orientation, sound attenuation through said plate means is greater than when said plate means is in a second orientation, wherein said plate means has a concave surface, a convex surface, a notched surface, or a grooved surface.

2. An acoustic earmuff device in accordance with claim 1, wherein said sound channel means is an interruption in said cup which provides at least a partially open pathway for cup leak or sound attenuation decrease.

3. An acoustic earmuff device in accordance with claim 2, wherein said interruption is a hole, a cut, an opening, a material having a lesser attenuation efficiency or a combination of the foregoing provided at least partially between the interior and the exterior of said cup.

4. An acoustic earmuff device in accordance with claim 1, wherein said plate means is a circular plate.

5. An acoustic earmuff device in accordance with claim 1, wherein said plate means is disposed on the interior surface of said cup, the exterior surface of said cup or between the interior and exterior surfaces of said cup.

6. An acoustic earmuff device in accordance with claim 1, wherein said plate means comprises a plastic, a metal, a foam, an elastomer or combination of the foregoing.

7. An acoustic earmuff device in accordance with claim 1, wherein said plate means includes at least one area of reduced sound attenuation.

8. An acoustic earmuff device in accordance with claim 7, wherein said said at least one area of reduced sound attenuation is a perforation, slit, hole, area of material having lower degrees of sound attenuation than the incident regions of said plate means, or combinations of the foregoing.

9. An acoustic earmuff device in accordance with claim 1, further comprising a biasing means operatively associated with said plate means.

10. An acoustic earmuff device in accordance with claim 9, wherein said biasing means initially biases said plate means in an orientation such that cup leak does not occur or sound attenuation is not decreased.

11. An acoustic earmuff device in accordance with claim 9, wherein said biasing means is a spring, foam, magnet, elastomer, stretchy material or other resilient member or combination of the foregoing.

12. An acoustic earmuff device in accordance with claim 1, wherein manipulation of said actuation means urges said plate means to an orientation which allows cup leak or decreased attenuation.

13. An acoustic earmuff device in accordance with claim 12, wherein manipulation of said actuation means is by depression of said actuation means, contact of two portions of said actuation means together, or rotation of said actuation means.

14. An acoustic earmuff device in accordance with claim 1, wherein said actuation means is a button, a post, a threaded post, a notched post, a screw, a pin, a plunger or combinations of the foregoing.

* * * * *